United States Patent [19]
Hof et al.

[11] Patent Number: 5,745,039
[45] Date of Patent: Apr. 28, 1998

[54] REMOTE STERILIZATION MONITOR

[75] Inventors: Craig R. Hof, San Salvador, Bahamas;
Gary Focarino, Flemington, N.J.;
Samuel David Lannigan, Philipsburg,
N.J.; Raymond A. Hof, Lawrenceville,
N.J.

[73] Assignee: Minnesota Mining and Manufacturing Company, St. Paul, Minn.

[21] Appl. No.: 803,740

[22] Filed: Feb. 21, 1997

[51] Int. Cl.⁶ ............................................. G08B 17/02
[52] U.S. Cl. .................. 340/590; 340/540; 340/584;
340/825.54; 374/160; 116/204; 116/217;
335/215
[58] Field of Search ................................ 340/590, 572,
340/540, 584, 825.54, 551; 374/160; 116/204,
217; 310/313 R; 335/215

[56] References Cited

U.S. PATENT DOCUMENTS

| | | | |
|---|---|---|---|
| Re. 32,428 | 5/1987 | Gregor et al. | 340/572 |
| Re. 34,515 | 1/1994 | Foley | 374/160 |
| 1,191,572 | 7/1916 | Davis | 206/63.3 |
| 3,174,716 | 3/1965 | Salter | 521/129 |
| 3,209,181 | 9/1965 | Brockman et al. | 310/26 |
| 3,313,266 | 4/1967 | Kelson | 116/114 |
| 3,341,238 | 9/1967 | White | 289/1.5 |
| 3,554,001 | 1/1971 | Norem | 374/14 |
| 3,652,249 | 3/1972 | White | 65/156 |
| 3,665,449 | 5/1972 | Elder et al. | 340/280 |
| 3,675,501 | 7/1972 | De Kanter | 374/170 |
| 3,684,737 | 8/1972 | Emigh | 252/408 |
| 3,696,679 | 10/1972 | Peterson et al. | 340/590 |
| 3,888,115 | 6/1975 | Schwartz | 73/765 |
| 3,938,125 | 2/1976 | Benassi | 340/572 |
| 3,981,683 | 9/1976 | Larsson et al. | 422/57 |
| 4,092,625 | 5/1978 | Newsom | 337/405 |
| 4,100,811 | 7/1978 | Cullen et al. | 73/654 |
| 4,138,216 | 2/1979 | Larsson et al. | 422/56 |
| 4,151,405 | 4/1979 | Peterson | 235/382 |
| 4,187,799 | 2/1980 | Zwarun | 116/217 |
| 4,216,401 | 8/1980 | Wagner | 310/313 R |
| 4,312,228 | 1/1982 | Wohltjen | 73/597 |
| 4,448,548 | 5/1984 | Foley | 374/160 |
| 4,510,489 | 4/1985 | Anderson, III et al. | 340/572 |
| 4,510,490 | 4/1985 | Anderson, III et al. | 340/572 |
| 4,591,566 | 5/1986 | Smith | 435/291 |
| 4,622,543 | 11/1986 | Anderson, III et al. | 340/572 |
| 4,644,286 | 2/1987 | Torre | 329/50 |
| 4,644,310 | 2/1987 | Anderson, III et al. | 335/215 |
| 4,647,910 | 3/1987 | Torre | 340/551 |
| 4,647,917 | 3/1987 | Anderson, III et al. | 340/572 |
| 4,658,241 | 4/1987 | Torre | 340/551 |
| 4,658,263 | 4/1987 | Urbanski | 343/788 |
| 4,660,025 | 4/1987 | Humphrey | 340/572 |
| 4,663,625 | 5/1987 | Yewen | 340/825 |
| 4,675,658 | 6/1987 | Anderson et al. | 340/551 |
| 4,685,461 | 8/1987 | Torre | 340/551 |
| 4,695,840 | 9/1987 | Darilek | 340/825.054 |

(List continued on next page.)

*Primary Examiner*—Jeffery Hofsass
*Assistant Examiner*—Benjamin C. Lee
*Attorney, Agent, or Firm*—Gary L. Griswold; Walter N. Kirn; Jeffrey J. Hohenshell

[57] ABSTRACT

A remote sterilization indicator is described. The indicator allows a sterilization cycle to be monitored without the need to visually inspect the indicator.

19 Claims, 6 Drawing Sheets

U.S. PATENT DOCUMENTS

| | | | |
|---|---|---|---|
| 4,746,830 | 5/1988 | Holland | 310/313 |
| 4,797,658 | 1/1989 | Humphrey | 340/551 |
| 4,850,716 | 7/1989 | Baker et al. | 374/160 |
| 5,051,726 | 9/1991 | Copeland et al. | 340/572 |
| 5,073,488 | 12/1991 | Matner et al. | 435/31 |
| 5,076,094 | 12/1991 | Frye et al. | 73/19.03 |
| 5,181,975 | 1/1993 | Pollack et al. | 152/152.1 |
| 5,189,397 | 2/1993 | Watkins et al. | 340/572 |
| 5,218,371 | 6/1993 | Copeland et al. | 343/742 |
| 5,252,144 | 10/1993 | Martis | 148/121 |
| 5,257,009 | 10/1993 | Narlow | 340/572 |
| 5,313,192 | 5/1994 | Ho et al. | 340/551 |
| 5,321,412 | 6/1994 | Kopp et al. | 343/742 |
| 5,327,118 | 7/1994 | Drucker et al. | 340/572 |
| 5,351,033 | 9/1994 | Liu et al. | 340/572 |
| 5,357,240 | 10/1994 | Sanford et al. | 340/572 |
| 5,463,376 | 10/1995 | Stoffer | 340/572 |
| 5,469,140 | 11/1995 | Liu et al. | 340/551 |
| 5,494,550 | 2/1996 | Benge | 156/268 |
| 5,495,230 | 2/1996 | Lian | 340/551 |
| 5,499,015 | 3/1996 | Winkler et al. | 340/551 |
| 5,537,094 | 7/1996 | Bettine et al. | 340/572 |
| 5,565,849 | 10/1996 | Ho et al. | 340/572 |
| 5,568,125 | 10/1996 | Liu | 340/551 |

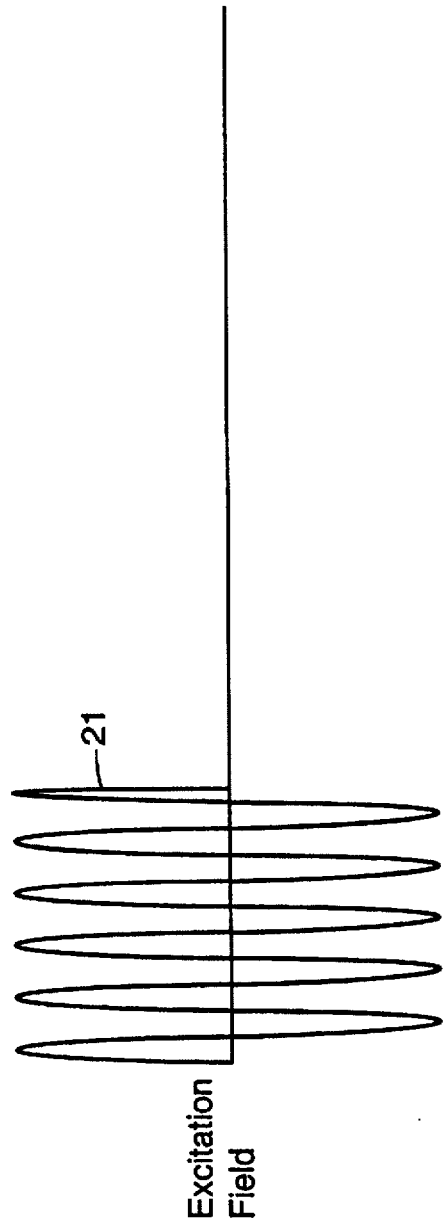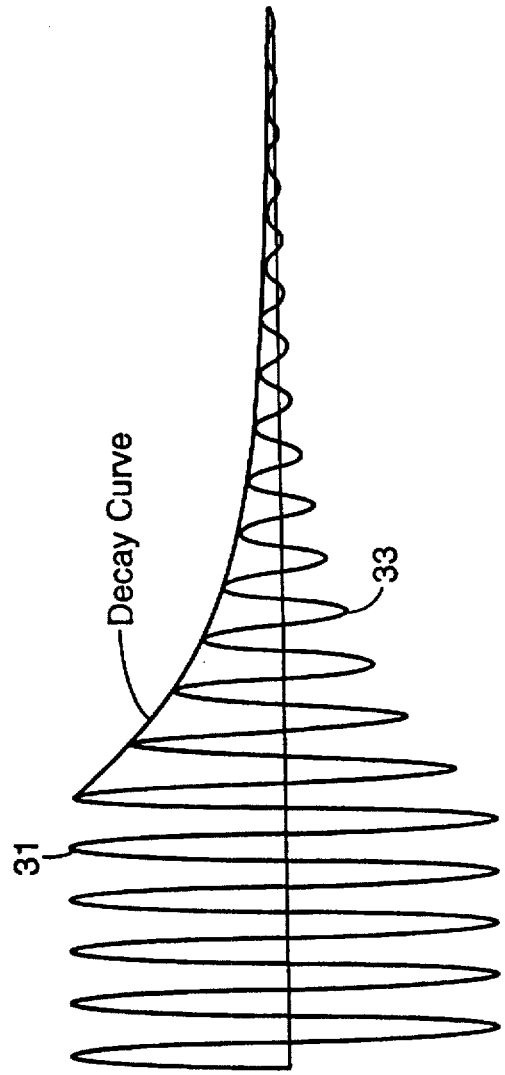

REMOTE STERILIZATION MONITOR

FIELD OF INVENTION

This invention relates to sterilization monitors. In particular the present invention relates to a sterilization monitor in which a change in the monitor caused upon predetermined exposure to a sterilization cycle is remotely detectable within an interrogation zone. The sterilization monitor is read remotely without the need to open a package containing sterilized goods.

BACKGROUND

Steam sterilizers or autoclaves remain in widespread use in modern hospitals. Initial attempts at monitoring the steam sterilization process relied on chemical type indicators. See for example, U.S. Pat. Nos. 3,313,266; 3,341,238 and 3,652, 249. These devices indicate whether the autoclave reached the melting point of the chemical in the tube for a time sufficient to melt the chemical.

Other sterilization process monitors rely on a temperature accelerated reaction to cause color change in an indicator. Though some of these devices purport to be operative at more than one temperature/time condition, they suffer from the disadvantage that they do not match the spore kill temperature/time relationship.

A successful chemical steam sterilization process monitor that mimics spore kill is described in U.S. Patent Reexamination Certificate No. B1—3,981,683, (Larsson et al.) the entire contents of the file histories of the patent and the Reexamination herein incorporated by reference. The Larsson et al. device comprises a backing strip, and a chemical compound whose normal melting point is above the sterilization temperature to be monitored. The chemical compound is mounted on the backing strip toward one end thereof. A wick contacts and extends away from the chemical compound toward a distal end of the backing strip. The device also includes a cover strip which is rate controlling with respect to the ingress of steam. The chemical compound is selected so that its melting point is depressed by the absorption of water passing through the cover strip in the vapor phase. Reissue U.S. Pat. No. 34,515 to Foley (incorporated herein by reference) discloses an improved chemical sterilization indicator that utilizes an acrylic adhesive.

Biological indicators are also used to monitor a sterilization process. Biological indicator devices are disclosed in U.S. Pat. No. 5,073,488.

With the Larsson et al. and Foley devices, a user typically must visually inspect the chemical indicator to read the indicator. The Larsson and Foley devices cannot remotely detect whether the desired temperature and humidity conditions necessary for proper sterilization were present during a particular steam cycle.

The art is also replete with electromagnetic surveillance systems for monitoring the presence or condition of a product in a particular zone. Electromagnetic surveillance systems typically include an interrogation means and a tag or a marker. These devices are particularly useful for deterring retail theft. Examples of such devices are described in U.S. Pat. Nos. 3,665,449; 3,696,679; 3,938,125, 4,151,405; 4,510,489; 4,510,490; 4,622,543; 4,644,286; 4,647,910; 4,647,917; 4,658,241; 4,658,263; 4,660,025; 4,675,658; 4,683,461; 4,746,830; 4,797,658; 5,051,726; 5,189,397; 5,218,371; 5,257,009; 5,313,192; 5,321,412; 5,327,118; 5,463,376; 5,495,230; 5,499,015 and 5,537,094 (the entire contents of each herein incorporated by reference). Tags or markers for use in such systems are also described in Reissue U.S. Pat. No. 32,428 and U.S. Pat. No. 5,494,550 (the entire contents of each of which are herein expressly incorporated by reference).

U.S. Pat. Nos. 4,510,489 and 4,510,490 disclose electronic article surveillance systems which utilize a magnetic element that mechanically vibrates at a predetermined frequency in response to an interrogation field at that frequency.

The vibration alters the magnetic permeability of the magnetic element, causing the magnetic element to produce a magnetic field at a predetermined frequency. That system and other prior art systems are believed to operate by sending an interrogation pulse or burst from an interrogation means. The interrogation pulse excites the marker into the mechanical resonance or oscillation. After the interrogation signal of the pulse or burst type is over, the marker undergoes damped oscillation at at least one resonant frequency. When the tag is within an interrogation zone, the vibrating marker will cause a voltage to be induced in a receiving coil in the interrogation means. When the marker frequency is sensed by a receiver, the receiver applies a signal to an indicator which indicates the presence of the marker. A commercial example of such an electromagnetic article surveillance system is believed to be the Ultra-Max brand EAS tag system available from Sensormatics of Deerfield Beach, Fla. U.S.A.

U.S. Pat. No. 4,850,716 discloses a remotely detectable sterilization monitor that, for the first time, successfully utilizes both sterilization assurance technology and electronic surveillance technology. That patent describes several different monitors each of which have a creating means for creating a remotely detectable magnetic response. The creating means have two distinct magnetic states: (1) a first state in which a first remotely detectable magnetic response is created upon a first interrogation and (2) a second state in which a second remotely detectable magnetic response (which is different than the first state) is created upon a second interrogation. The monitor includes a material which melts upon being heated to a predetermined temperature for changing the creating means from the first to the second state upon melting.

SUMMARY OF THE INVENTION

The present invention comprises a remotely detectable sterilization process monitor for use with an interrogation mechanism. The interrogation mechanism is capable of interrogating the monitor by providing a pulsed, excitation magnetic field within an interrogation zone. The interrogation mechanism is also capable of detecting an identity signal provided by the monitor.

The monitor comprises a strip of magnetostrictive ferromagnetic material that mechanically resonates when interrogated by the interrogation mechanism. The monitor also includes a magnetic material capable of magnetically biasing the strip of magnetostrictive ferromagnetic material to arm the magnetostrictive ferromagnetic material to provide an identity signal. After the pulse of the excitation magnetic field of the interrogation mechanism ends, the magnetostrictive material resonates within the magnetic bias provided by the magnetic material in a decaying fashion to provide the identity signal to the interrogation mechanism. A receiver or other electronic circuitry may then indicate the presence of the monitor within the interrogation zone.

The monitor also includes a clamping means for physically holding the magnetostrictive ferromagnetic material such that the magnetostrictive ferromagnetic material is not allowed to resonate when interrogated by the interrogation mechanism, even when the monitor is within the interrogation zone.

The clamping means preferably comprises a meltable organic compound. Upon exposure of the monitor to predetermined conditions, the organic compound melts sufficiently to allow the magnetostrictive ferromagnetic material to resonate when interrogated by the interrogation mechanism.

Alternatively, the present invention may be described as a remote monitor comprising creating means for creating a remotely detectable magnetic response. The creating means comprises a magnetic material of high permeability and low coercivity. The creating means has at least two distinct magnetic states: (1) a first state in which a first remotely detectable magnetic response is created upon interrogation, and (2) a second state in which a second remotely detectable magnetic response which is different from the first state is created upon interrogation. In this description of the invention, the sterilization monitor comprises clamping and release means for holding the creating means in the first state. The clamping and release means include a spring clamp for holding the creating means in the first state and a material which melts upon being heated to a predetermined temperature for changing the creating means from the first to the second state upon melting. The spring clamp is preferably separate and distinct from the magnetic material of high permeability and low coercivity.

The present invention may also be described as a method of monitoring a sterilization process using a remotely detectable sterilization monitor. The sterilization process may be monitored without the need to visually inspect the sterilization monitor.

BRIEF DESCRIPTION OF THE DRAWINGS

The present invention will be further described with reference to the accompanying drawing wherein like reference numeral refer to like parts in the several views, and wherein:

FIG. 1 is a graph believed to show an example of characteristics of an excitation field that may be provided by an interrogation unit for use with the present invention;

FIG. 2 is a graph believed to show characteristics of the field generated by the sterilization monitor, including the result of the excitation field provided by the interrogation unit (see FIG. 1) and the resultant decay curve generated upon termination of the excitation field provided by the interrogation unit;

DETAILED DESCRIPTION

Referring now to FIGS. 6–9, there is shown a preferred embodiment of sterilization monitor 10 according to the present invention. While it is believed that the monitor may be constructed to monitor a variety of sterilization cycles (e.g. ethylene oxide cycles, vapor and liquid phase hydrogen peroxide or peracetic acid cycles, and plasma cycles), the monitor 10 is particularly suitable for monitoring steam sterilization processes. The monitor 10 frees the user from the necessity of visually inspecting a monitoring device to determine whether a monitor 10 has been subjected to predetermined conditions indicative of sterilization conditions. There is little or no need to open a package containing goods subjected to a sterilization cycle, as the package may be read electronically.

The sterilization monitor 10 is particularly suitable for use with an interrogation mechanism 20 that uses components from conventional, readily available, relatively inexpensive electronic article surveillance systems. Referring now to FIGS. 1–4, the interrogation mechanism 20 preferably interrogates the monitor 10 by providing a pulsed or burst excitation magnetic field (e.g. at a preselected frequency) within an interrogation zone 22. The interrogation mechanism 20 detects an identity signal provided by the monitor 10.

Figure 3:
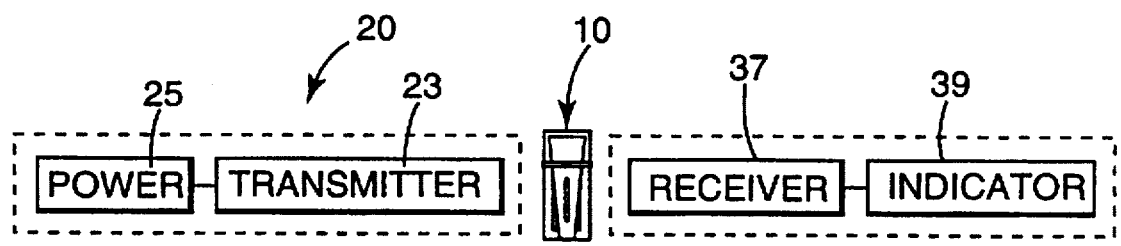
FIG. 3 is a schematic diagram of elements of an interrogation unit for use with the present invention.
Figure 4:
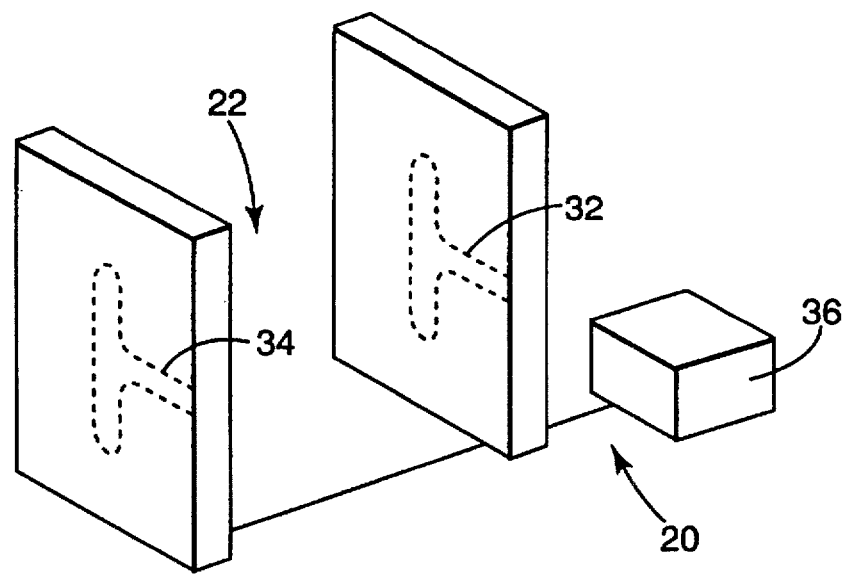
FIG. 4 is a schematic view of an interrogation unit for use with the present invention.

FIG. 3 shows some of the elements of the interrogation mechanism 20. Preferably, the interrogation mechanism 20 is of the type described in U.S. Pat. Nos. 4,510,489 and 4,510,490 (the entire contents of each of which is herein incorporated by reference). The interrogation mechanisms disclosed in those patents are designed for use with a marker or tag or monitor having a magnetic element that mechanically vibrates at a predetermined frequency in response to an interrogation field (e.g. at that frequency). Markers for use with such interrogation mechanisms are described in those patents as well as U.S. Pat. Nos. 5,252,144; 5,351,033; 5,357,240; 5,469,140; 5,565,849 and 5,568,125 (the entire contents of each of which are herein incorporated by reference).

FIG. 1 is a graph of what is believed to be some characteristics of a typical interrogation magnetic field or excitation magnetic field 21 provided by a transmitter 23 of the interrogation mechanism 20 described above. The excitation magnetic field 21 is preferably provided by a coil 32 (see FIG. 4). The interrogation magnetic field 21 is in the form of an interrogation pulse or burst. The transmitter 23 is powered by a suitable power source 25. For example, a pulsed AC magnetic field may be generated at about 53 KHz.

The excitation magnetic field 21 is believed to excite a magnetic element of the monitor 10 into mechanical vibration (preferably at a predetermined frequency). The vibration is believed to alter the magnetic permeability of the monitor (e.g. a magnetic element), causing the magnetic element to produce a magnetic field at a predetermined frequency. FIG. 2 is a graph which is believed to illustrate the response of the monitor 10 in the presence of the excitation magnetic field 21. The first portion 31 of the graph in FIG. 2 illustrates the signal from the monitor 10 in the presence of the excitation magnetic field 21. When the pulse of the excitation magnetic field 21 ends, the dimensional oscillation of the monitor 10 stops and the monitor 10 undergoes damped oscillation at at least one resonant frequency. The amplitude of the monitor signal decays over time to zero. The particular shape of the decay curve 33 is believed to provide an identity signal to the interrogation mechanism 20.

Between pulses of the excitation field 21, the interrogation mechanism 20 is believed to sense the particular decay signal 33 from a monitor 10. For example, the identity signal may be sensed in a coil 34 in the interrogation mechanism 20. The interrogation mechanism utilizes a receiver 37 (including coil 34, for example) for sensing the decay or identity signal 33 from the monitor. An indicator 39 indicates whether the decay signal 33 was received.

When the monitor frequency is sensed by the receiver 37, the receiver applies a signal to the indicator 39 which optionally can record the presence of the monitor 10. Suitable electronic circuitry 36 controls the interrogation mechanism 20. Commercial examples of the above described electromagnetic article surveillance system are believed to be the Ultra-Max brand EAS tag systems available from Sensormatics of Deerfield Beach, Fla. U.S.A.

Figure 6:
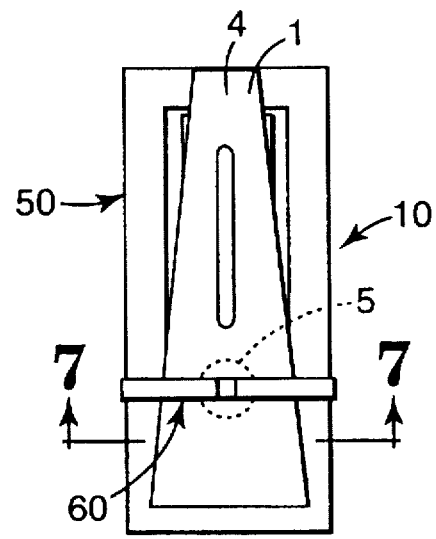
FIG. 6 is a top view of an assembled sterilization monitor according to a first embodiment the present invention.
Figure 7:
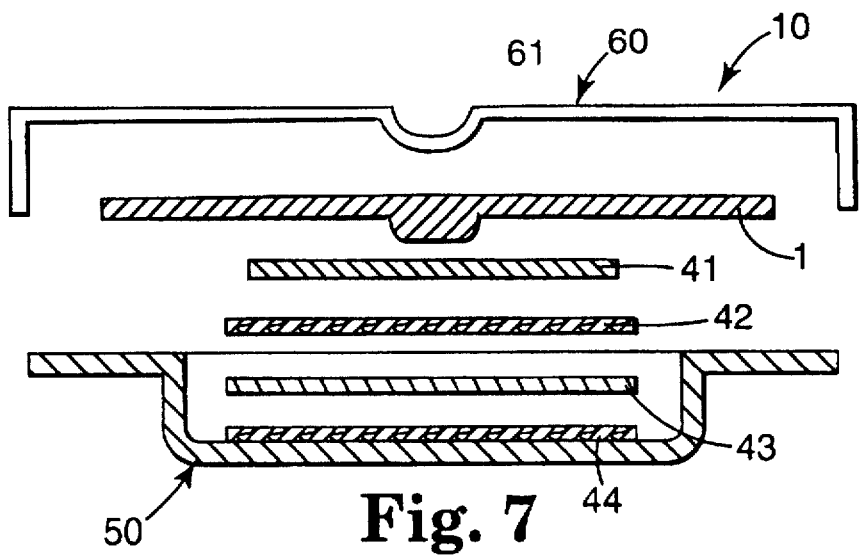
FIG. 7 is an exploded, partially sectional view of the sterilization monitor of FIG. 6 taken approximately along lines 7—7 of FIG. 6, with parts disassembled to illustrate details.

Referring now to FIGS. 6 and 7, the monitor 10 preferably comprises a strip of magnetostrictive ferromagnetic material 41 adapted to mechanically resonate when interrogated by the interrogation mechanism 20. The monitor 10 also includes a magnetic material 43 capable of magnetically biasing the strip of magnetostrictive ferromagnetic material 41 to arm the magnetostrictive ferromagnetic material 41 to provide an identity signal 33. After the pulse of the excitation magnetic field 21 of the interrogation mechanism 20 ends, it is believed that the magnetostrictive material 41 resonates within the magnetic bias provided by the magnetic material 43 in a decaying fashion to provide the identity signal 33 to the interrogation mechanism 20.

Figure 5:
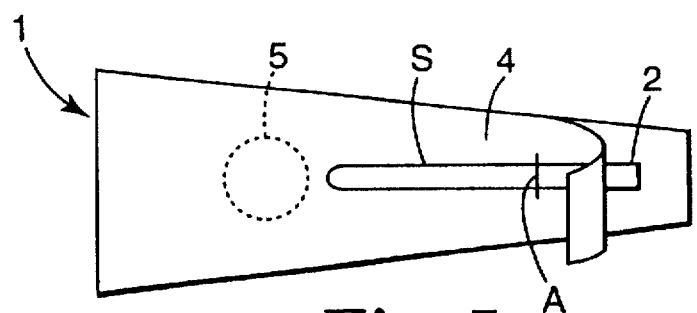
FIG. 5 is a plan view of a portion of a first embodiment of sterilization monitor according to the present invention which includes a meltable organic compound.

The monitor 10 also includes clamping means for physically holding the magnetostrictive ferromagnetic material 41 such that the magnetostrictive ferromagnetic material 41 is not allowed to resonate when interrogated by the interrogation mechanism 20. Referring to FIG. 5, the clamping means preferably comprises an organic compound 5. Upon exposure of the monitor 10 to at least a portion of a sterilization cycle (and preferably the entire sterilization cycle), the organic compound 5 melts sufficiently to release the magnetostrictive ferromagnetic material 41 to allow the material 41 to resonate when interrogated by the interrogation mechanism 20. Preferably, the organic compound 5 is housed in a first assembly 1.

Referring now to FIG. 5, the first assembly 1 preferably comprises a package containing a wick 2 a pellet of the organic compound 5 mounted thereon. The wick 2 and organic compound 5 are preferably sealed in an assembly that includes a rate controlling film 4 and a backing (e.g. aluminum).

The organic compound 5 is a temperature/steam sensitive material. Preferably, the organic compound 5 is any of the known compositions having the property that their melting points are depressed in the presence of saturated steam into the temperature range typical of the sterilization equipment, but normally are higher than such temperatures. The melting of the organic compound indicates the presence of steam at a minimum temperature. Suitable materials are taught in U.S. Pat. No. 3,981,683 (Larsson et al.) and its Reexamination Certificate No. 3,981,683 B1 (the entire contents of each of which are herein incorporated by reference). As an example not intended to be limiting, the organic material 5 may be a compound selected from the group consisting of 2-chloroacetamide, 2-ethoxybenzamide, benzoic acid, diphenyl succinate, dichlorophenol, dimethyl phenol, benzamide, urea, 1,4 dihydroxybenzophenone, hydroquinone, dioxime, ethylene ester of tuluene sulfonic acid, salicylamide, salicylic acid, and 1,8-octane dicarboxylic acid.

The compound 5 selected should have a normal melting point about 5 to about 50 degrees F. greater than the temperature of the monitored steam sterilization process; typically, about 8 to about 40 degrees F. For example the range may be from about 10 to about 30 degrees F. greater than the temperature of the monitored steam process, more preferably about 20 degrees F. greater.

That water be soluble in the organic compound 5 to a slight extent is preferable to the operation of the monitor 10, particularly when a steam cycle is monitored. Not wishing to be bound by theory, it is believed that the water acts as a melting point depressant. The object in selecting an organic compound 5 having a melting point higher than the temperature to be monitored, but capable of having its melting point depressed by the absorption of water is to contribute to a feature of the present invention wherein the material 5 will not melt in the absence of water vapor at the control temperature. The phrases "control temperature" and "organic compound" as used in the present specification and claims are used in the same manner as their use in Larsson et al. U.S. Pat. No. 3,981,683.

Though it is possible to determine the actual degree of water solubility in the organic compound 5, it is not essential. The compound preferably contains functional groups which will result in a degree of water solubility. Illustrative, non-limiting examples of the functional groups which the organic compound 5 preferably contain are aldehyde, carbonyl, ester, keto, ether, hydroxy, amino, amide, carboxy, phosphate, phosphonate sulfones, sulfate, sulfonate, etc., and mixtures thereof. Other suitable compounds are taught in Larrson et al. U.S. Pat. No. 3,981,683.

The melting time of the organic compound 5 may optionally be controlled in the manner taught by U.S. Pat. No. 4,448,548 (the entire contents incorporated by reference). A binder may be added to the material 5 to allow it to be shaped into tablet form with the added benefit of delay in the melting time of the entire tablet as the percentage of binder increases. For example, polyvinylpyrrolidone (PVP) may be added. The tablet may contain other materials desirable for mass production efficiency or other reasons.

The wick 2 may be any suitable material through which the organic compound 5 can migrate (e.g. by capillary action). The preferred wick 2 is a paper strip. Other wicking means such as non-woven polymeric fabrics and inorganic fibrous compositions may be used.

The dimensions of the wick 2 are not essential. However, the dimensions of thickness and width may affect the rate of wicking and determine the quantity of organic compound 5 required to result in a suitable monitor 10 and in a suitable optional scale length A (discussed below). The wick 2 is preferably as thin a practical. A suitable width for the wick 2 is about 3/16 to about 1/8 of an inch e.g. 1/4 inch in width.

Illustrative, non-limiting examples of the materials useful as wicks 2 are Whatman Nos. 1, 5, 114 and 5410 filter papers, Schleicher & Scheull (S&S) No. 410, 593 & 598 papers, supported microcrystalline cellulose (TLC plate), supported aluminum oxide, and supported silica gel.

Alternatively, the wick 2 may be omitted from the present invention as the sterilization monitor 10 is designed to monitor a sterilization process or cycle without the need to visually inspect a color bar or scale which might require opening the package containing the goods and the monitor 10 subjected to a steam cycle. However, even where no visual evidence of sterilization is desired, it is preferred that a paper layer be placed under the organic compound 5 to absorb the compound as it melts.

The rate controlling film 4 of the first assembly 1 permits moisture (gaseous) to pass through at rate sufficient to depress the melting point of the organic compound 5 (e.g. to the sterilization temperature to be monitored). The vapor transmission rate may depend upon the operating temperature of the sterilizer and the organic compound 5. The vapor transmission rate as a function of temperature for various films and the effect of water vapor on melting point depression of various compounds may be determined. These data may then be used to select combinations of first assembly 1 materials.

The rate controlling film 4 should be stable in the presence of the compound 5 under operating conditions. For example, (polyethyleneglycol terephthalic acid ester) should be avoided where the organic compound is a hydroxy containing aromatic compound, e.g. alkyl substituted phenols. Illustrative examples of suitable rate controlling films are mylar, polypropylene, polystyrene and polymethylmethacrylate.

Optionally, the rate controlling film 4 may be transparent and clear to afford visual inspection of the progress of the organic compound as it wicks along the wick 2. A preferred rate controlling film material is polypropylene since it has a high softening point and is relatively inert to most chemical compounds. Additionally, it has an acceptable water vapor transmission rate at temperatures about 250 degrees F. to 270 degrees F., the temperature at which hospital sterilization processes are typically carried out.

The thickness of the rate controlling film 4 will affect the water vapor transmission rate. Preferably, cast polypropylene film having a thickness of about 1 to about 8 mils, more preferably about 2 mils, is used.

The term "rate controlling" when used in the specification and claims with respect to the rate controlling film means that the film controls the water vapor transmission rate by virtue of its permeability to water vapor at the temperature to be monitored. No effort is made to determine the actual vapor transmission rate or in any other way to control the vapor transmission rate.

The first assembly 1 is placed in a container 50 that preferably includes a first paper strip 42, the magnetostrictive ferromagnetic material 41, a second paper strip 44 and the magnetic material 43. The container 50 is designed to withstand the conditions of a sterilization cycle. For steam sterilization, the container 50 is preferably made from an amorphous polyester which is vacuum molded, and subsequently annealed in a 270 degrees F. autoclave. The material for the container 50 should be dimensionally stable during the sterilization process. Containers used in preparing prototype monitors were manufactured by Mullinex Packaging, Inc. of Fort Wayne, Ind.

Figure 8:
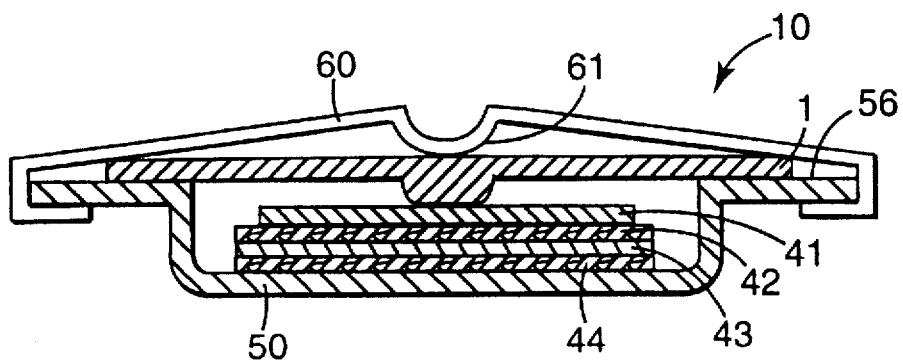
FIG. 8 is a sectional view of the sterilization monitor of FIG. 6 prior to monitoring a sterilization process.
Figure 9:
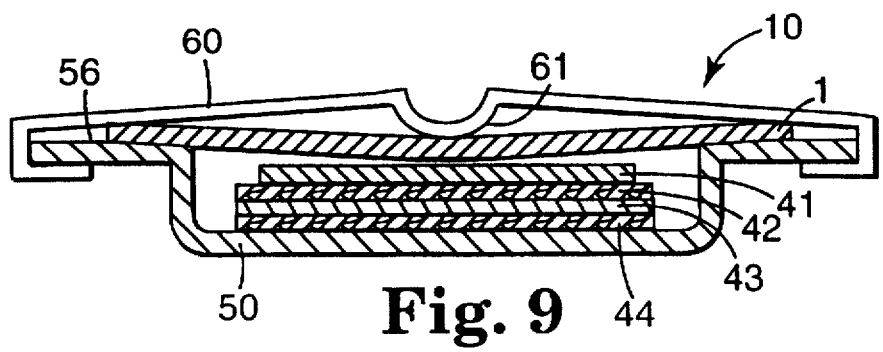
FIG. 9 is a sectional view of the sterilization monitor of the present invention after monitoring a sterilization process.
Figure 10:
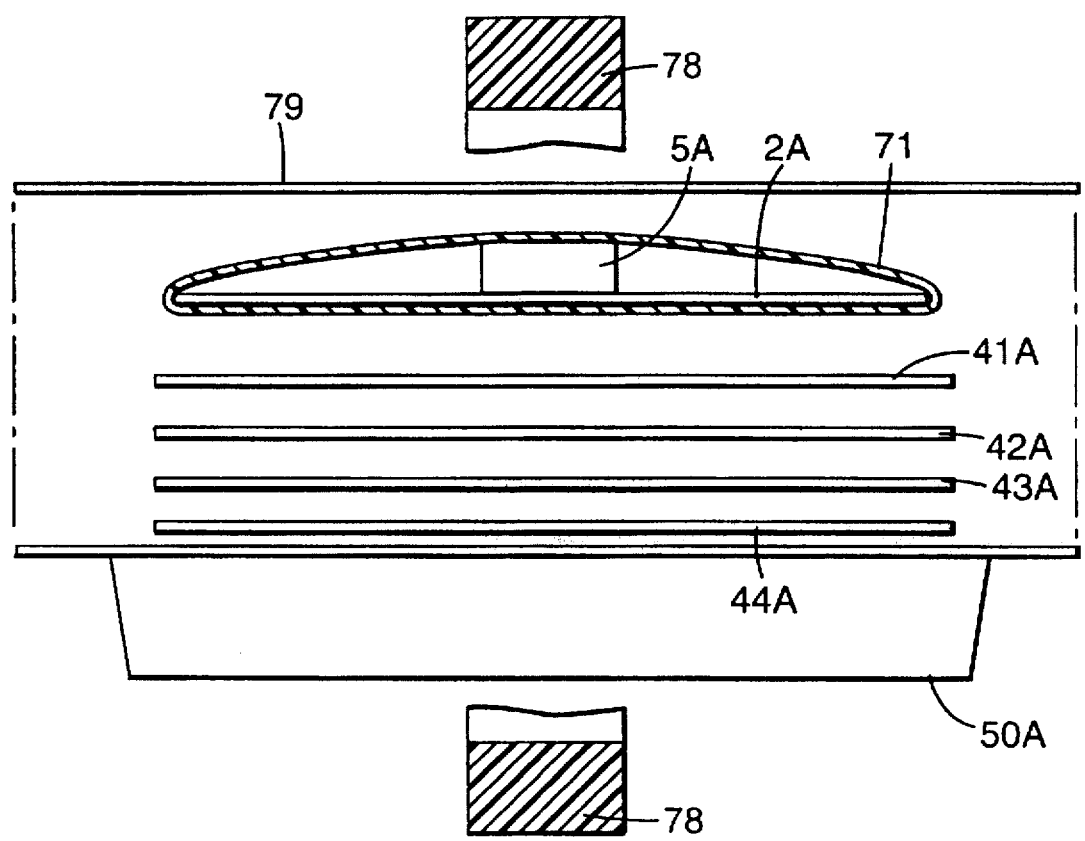
FIG. 10 is an exploded, partial sectional view of a second embodiment of sterilization monitor according to the present invention, with the parts disassembled to illustrate details.
Figure 11:
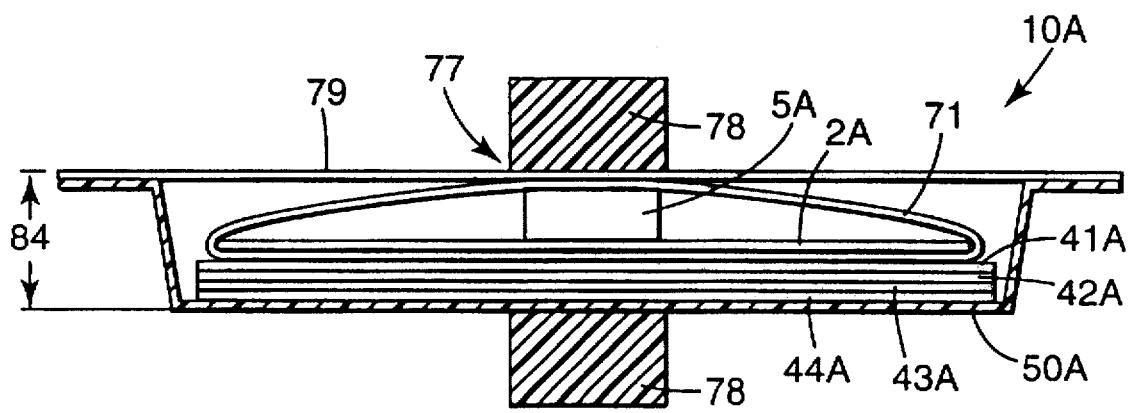
FIG. 11 is a section view of the sterilization monitor of FIG. 10 prior to monitoring a sterilization process.

Referring now to FIGS. 8 and 9, the clamping means for the monitor 10 preferably comprises a spring clamp 60. The spring clamp 60 is movable between a first position (e.g. FIG. 8) and second position (FIG. 9) that is spaced from the first position. In the first position, the spring 60 provides a bias through the organic material 5 which physically holds the magnetostrictive ferromagnetic material 41 such that the magnetostrictive ferromagnetic material 41 is not allowed to resonate when interrogated by the interrogation mechanism. It is noted that other factors may contribute to the lack of resonation of the material 41 in this position, such as any magnetic attraction between the material 43 and the material 41. In the second position, the force of the spring 60 is released sufficiently to allow the magnetostrictive ferromagnetic material 41 to resonate when interrogated by the interrogation mechanism.

FIG. 8 illustrates the sterilization monitor 10 prior to undergoing a sterilization cycle or process. In this position, the spring clamp 60 is designed to physically hold or bias the magnetostrictive ferromagnetic material 41 to prevent it from resonating in the event that the monitor 10 is interrogated by the interrogation mechanism. The spring bias acts through the first assembly 1 (including the organic material 5) and clamps the material 41 against the paper 42.

FIG. 9 illustrates the sterilization monitor 10 after the monitor 10 was subjected to a sterilization cycle (e.g. preferably a complete sterilization cycle). During the sterilization cycle, the organic material 5 melted which results in the release of the material 41. After the organic material 5 melts, the spring clamp 60 relaxes its force or physical hold on the magnetostrictive ferromagnetic material 41 sufficient to allow the material 41 to resonate when interrogated by the interrogation mechanism 20.

Various mechanisms may be utilized to prevent the spring clamp 60 from physically holding the magnetostrictive ferromagnetic material 41 after the material 5 melts. For example, in the depicted embodiment, as the material 5 melts, a rib portion 61 of the spring clamp 60 moves toward the ferromagnetic material 41. During the melting of the material 5, the end portions of the spring clamp 60 engage portions of the first assembly 1 and top shelf portions of the container 50. This engagement acts as a barrier to further deflection of rib portion 61 of the spring clamp 60 toward the material 41. Other mechanisms will be apparent to those skilled in the art such as spring interrupt mechanisms.

To determine whether goods including the process monitor 10 were exposed to an acceptable sterilization cycle, the goods and monitor 10 are placed in an interrogation zone 22. If the organic compound 5 melted sufficiently to indicate sterilization, the interrogation mechanism 20 will preferably provide an audible signal. Otherwise, it is presumed that the goods have not been exposed to an acceptable sterilization cycle. A suitable device used to define the interrogation zone 22 is a Double Checker Model No. ZB150, available from Sensormatics, Inc. of Deerfield Beach, Fla.

The sensitivity of the monitor 10 may be modified in several different manners. For example, the size, shape and composition of the material 5 may be modified to control the sensitivity of the monitor 10. The sensitivity may also be addressed by modifying the characteristics of the wick 2 and the rate controlling film 4.

The monitor 10 is particularly suitable for use in a method of monitoring a steam sterilization process comprising the step of providing an interrogation mechanism 20 capable of interrogating the monitor 10 and capable of detecting an identity signal provided by the monitor 10. The interrogation mechanism 20 is typically equipped to provide an interrogation zone 22. For example, the interrogation mechanism 20 may be installed in a hospital or surgical center suite which houses steam sterilizers. Alternatively, the interrogation mechanism 20 may be installed in situ in a steam sterilizer.

The interrogation mechanism 20 preferably utilizes components from a conventional, readily available, relatively inexpensive, electronic article surveillance system such as the Double Checker, model no. ZB 150, available from Sensormatics of Deerfield Beach, Fla. It is believed Double Checker device has a transmitter for providing a pulsed or burst AC magnetic field at a preselected frequency (e.g. 53 kHz) similar to that shown in FIG. 1.

The method also includes the step of providing a monitor 10 comprising a strip of magnetostrictive ferromagnetic material 41, and a magnetic material 43 capable of magnetically biasing the strip of magnetostrictive ferromagnetic material 41 to arm the magnetostrictive ferromagnetic material 41 to provide the identity signal, clamping means 60 for physically holding the magnetostrictive ferromagnetic material 41 such that the magnetostrictive ferromagnetic material 41 is not allowed to resonate when interrogated by the interrogation mechanism 20. The clamping means comprises a meltable compound 5.

The method includes the step of exposing the sterilization monitor 10 to at least a portion of the steam process to be monitored. Preferably the monitor 10 is exposed to the entire steam process. For example, the monitor 10 may be placed with goods to be sterilized (e.g. bowls, pans etc.) and then bundled in several layers of cloth. The bundle is then subjected to a steam sterilization cycle. After a predetermined exposure to the steam sterilization process to be monitored, the organic compound 5 melts sufficiently to release the clamping means 60 to allow the magnetostrictive ferromagnetic material 41 to resonate when interrogated by the interrogation mechanism 20.

The rate of melting of the organic material 5 as well as the kill rate of microbes results from an integration of time and temperature so that the monitor 10 is useful in a variety of temperatures. In particular, the time required for the meltable material 5 to move a certain fixed distance along the wick paper in the first assembly 1 is very temperature dependent. The same generally holds for the kill time of microbes. When a color front on the strip reaches a certain position on the first assembly 1, such as that indicated at A in FIG. 5, it is assumed that the environment has undergone proper sterilization (the goods are accepted), i.e., the probability that all of the microbes present have been killed is, for example, 0.99999.

Optionally, the first assembly 1 may include printing A near a slot which provides for a visual indication of the strip. The printing may comprise a line and the terms "Accept" and "Reject" on opposite sides of the line. Preferably, the monitor 10 is designed such that, just after the organic compound 5 wicks past the "Accept" line, the clamping means 60 releases the magnetostrictive ferromagnetic material 41 sufficiently to allow the material 41 to resonate when interrogated by the interrogation mechanism.

As used herein, the "predetermined exposure" or the amount of melting of the material 5 sufficient to release the clamping means 60 preferably at least roughly coincides with the amount of melting required to indicate that the sterilization cycle has undergone proper sterilization, i.e., the probability that all of the microbes present have been killed is, for example, 0.99999. As discussed above, however, the sensitivity of the monitor 10 may be manipulated to provide greater or lesser challenges to the sterilization cycle (e.g. for an early warning of sterilizer inefficiencies).

Both the rate of melting of the compound 5 and the fraction of the compound 5 required to melt for the electronic indication to be detected can be adjusted. Increasing the mass of the compound 5 will generally increase the time required to signal. Increasing the thickness of the rate controlling film 4 will also increase the time required to signal. The inverse are also generally true. The monitor 10 may also be tuned by adjusting the wick paper 2 (e.g. composition, width or thickness) or the rate controlling film 4 (e.g. composition, width or thickness).

After the above steps are taken, the method includes the step of interrogating the monitor 10 in the interrogation zone 22 by providing a pulsed, excitation magnetic field at a frequency in the interrogation zone 22. If the clamping means 60 is released, after the pulse of the excitation magnetic field of the interrogation mechanism ends, the magnetostrictive material 41 resonates within the magnetic bias provided by the magnetic material 43 in a decaying fashion to provide the identity signal to the interrogation mechanism 20. For example, after the sterilization cycle, an operator may pass the monitor 10 or the entire bundle (including the monitor) through the interrogation zone 22 and wait for a response. In the example above where the interrogation mechanism 20 comprises a Double Checker (model no. ZB 150) device, the excitation magnetic field 21 excites the monitor 10 into mechanical vibration. FIG. 2 is believed to generally illustrate the response of the monitor 10 in the presence of the magnetic field 21. When the pulse of the excitation magnetic field 21 ends, the dimensional oscillation of the monitor 10 ends and the monitor 10 undergoes damped oscillation. The amplitude of the monitor signal decays over time to zero. The particular shape of the decay curve 33 provides the identity signal to the interrogation mechanism 20.

The method also includes the steps of detecting the identity signal with the interrogation mechanism 20; and indicating to the operator whether the identity signal was detected by the interrogation mechanism 20. The interrogation mechanism 20 may be programmed to provide an audible and/or visual signal (e.g. a beep sound and/or a green light) upon detecting the identity signal. In this manner, an operator may be given an indication of the efficacy of the sterilization cycle without the need for unwrapping a bundle and visually inspecting the monitor 10. Alternatively, as discussed above, the first assembly 1 of the monitor 10 is preferably provided with printing near a slot for visually indicating whether the sterilization cycle has passed the challenge (e.g. whether the goods subjected to the cycle should be accepted or rejected). This visual indication may serve as a backup or secondary source of information for the user.

While the present invention is preferably used with an interrogation mechanism of the type described in U.S. Pat. Nos. 4,510,489 and 4,510,490, it should be noted that the present invention could be utilized in different interrogation mechanisms, such as for example, some of the interrogation mechanisms of the electronic article surveillance systems described in the BACKGROUND portion of this document.

In an alternative description, the present invention comprises an improvement to the devices disclosed in U.S. Pat. No. 4,859,716. In this characterization, the monitor 10 comprises a creating means for creating a remotely detectable magnetic response. The creating means includes a magnetic material of high permeability and low coercivity. Preferably, the creating means includes a magnetostrictive ferromagnetic material 41 and a magnetizeable material 43. The creating means has at least two distinct magnetic states: (1) a first state in which a first remotely detectable magnetic response is created upon a first interrogation, and (2) a second state in which a second remotely detectable magnetic response which is different from the first state is created upon a second interrogation. For example, the first state may be that shown in FIG. 8 and described above, and the second state may be that shown in FIG. 9 and described above. The first and second interrogations may be provided by the interrogation mechanism 20 described above (e.g. utilizing elements from the Ultra-Max brand EAS tag systems from Sensormatics, such as the Double Checker, model no. ZB 150). Alternatively, the monitor 10 may be constructed for use with other existing interrogation mechanisms constructed from electronic article surveillance systems such as those described above in the BACKGROUND section of this document.

In this description of the invention, the monitor 10 includes clamping and release means 60 for holding the creating means in the first state (see FIG. 8). The clamping and release means 60 includes a spring clamp for holding the creating means in the first state (FIG. 8) to restrict the creating means from entering the second state (FIG. 9), and an organic material 5 which melts upon being heated to a predetermined temperature for changing the creating means from the first to the second state upon melting. Preferably, the spring clamp is separate and distinct from the magnetizeable material 43 and the magnetostrictive ferromagnetic material 41, as opposed, for example, to a clamping and release means comprising pressure exerted due to the inherent resilience of a deflected material (e.g. the magnetizeable material 43 or the magnetostrictive ferromagnetic material 41). A spring clamp which is separate and distinct from the magnetizeable material and the magnetostrictive ferromagnetic material provides advantages in the construction, manufacturing and assemblage of the monitor 10. The present invention may also be viewed as a method of monitoring a sterilization cycle utilizing a monitor as described in this alternate description of the monitor 10.

EXAMPLE 1

With reference to FIGS. 5–9, sterilization monitors 10 were prepared in the following manner. The first assembly 1 was prepared using commercially pure annealed aluminum as a backing strip and Schleicher & Schuell paper designated by the manufacturer as S&S-593 as wick paper 2. The aluminum had a thickness of about 0.0030 inches and a length of about 2.03 inches. The width of the aluminum tapered from about 0.85 inches to about 0.40 inches. The wick paper 2 was about 0.125 inches×1.25 inches, with a thickness of about 0.006 inches.

The material or compound 5 comprised pure salicylamide with additives in tablet form. The compound 5 was placed between the aluminum and a portion of the wick paper 2. Adhesive coated on the aluminum adhered the compound 5 to the aluminum. The adhesive comprised Isotac acrylic adhesive, available from 3M of St. Paul, Minn. Alternatively, the wick paper 2 may be placed between the compound 5 and the aluminum. The placement of the wick paper 2 can have the effect of altering the rate of steam permeation. Steam permeates and supplies water to the compound 5 when there is a path from the point of permeation to the compound 5. By placing the wick paper 2 next to the rate controlling film 4, the wick paper 2 may provide such a path.

The compound 5 comprised pure salicylamide mixed a Zapon Black X-50 dye (0.2%) available from BASF, and a 399 magnesium silicate talc available from Whitaker, Clark & Daniels (1.5%). The compound 5 was in a hollow cylindrical form (e.g. doughnut shaped) with an outer diameter of about 0.189 inches and with a hole or bore of about 0.085 inches in diameter. The compound 5 had a height of about 0.054 inches.

The aluminum, wicking paper 2 and compound 5 were covered with a rate controlling film 4 comprising Exxon Extrel 27 non-oriented polypropylene with a thickness of about 2 mil., a length of about 2 inches and a width of about 0.85 inches tapering to about 0.415 inches. A paper covered the rate controlling film 4 except for a narrow slot S. The paper comprised Avery label stock. The rate controlling film 4 and the aluminum had dimensions approximately the same (except thickness). The paper cover had approximately the same dimensions as the aluminum except that the paper cover had the slot S. The Avery label stock is laid upon the polypropylene rate controlling film to make a subassembly. The label stock was adhered to the rate controlling film by a suitable pressure sensitive adhesive on the label stock. The acrylic adhesive (3M Isotac adhesive) is located on the aluminum and adheres the compound 5 and wick to the aluminum. The subassembly is then laid upon the aluminum/compound 5, wick paper 2 and the adhesive, label stock to the outside (away from the adhesive on the aluminum), and the adhesive binds the rate controlling film 4 to the aluminum.

The metal clip portion of the clamp means 60 was constructed from a type 301 stainless steel strip, Alloy heat #121225, Edge #3 Temper SPG, available from Gibbs Wire and Steel Company. The outer axial length (with approximately 0.13 inch container grasping loop portions formed therein) of the clip was approximately 1.13 inches. The width of the clip was about 0.13 inches and the thickness of the clip was approximately 0.007 inches. The depth of rib 61 was about 0.080 inches.

The container 50 comprised amorphous CPET with a thickness of about 0.02 inches. The shoulder portion 56 (designed to engage the distal ends of the clamp means 60) of the container 50 was about ¼ inches wide along each edge of the cavity. The cavity had a length of about 1.7 inches and a width of about 0.6 inches and a depth of about 0.115 inches. The container was constructed by Mullinex Packages, Inc.

The magnetostrictive ferromagnetic material 41 comprised 2826 Metglas available from Sensormatics, Inc. of Deerfield Beach, Fla. The composition and other characteristics of that material are believed to be described documents in the file history of Reissue U.S. Pat. No. 32,428 (the entire contents of which are herein incorporated by reference) which comprises the reissue of U.S. Pat. No. 4,484,184. Those documents are believed to include the Egami et al. article entitled, AMORPHOUS ALLOYS AS SOFT MAGNETIC MATERIALS, AIP Conference Materials (1975). The material 41 had a length of about 1.45 inches, a width of about 0.5 inches and a thickness of about 3 mil. (0.002 inches). The first paper layer 42 comprised Whatman #1 paper with a length of about 1.65 inches, a width of about 0.55 inches and a thickness of about 6 mil. (0.006 inches). The paper layer 42 is believed to act as a spacer between the materials 41 and 43 to afford efficient operation of the device 10. It was found that without the paper 42, water was apt to condense on the magnetostrictive ferromagnetic material 41 and magnetic material 43, deleteriously affecting the operation of the monitor 10. The paper layer 42 also helps prevent dampening of the magnetostrictive ferromagnetic material's 41 vibration due to magnetic attraction between material 43 and material 41 by providing space between the materials 41 and 43. Alternatively, other means for reducing the chances of condensation may be utilized. For example, any water absorbing material, synthetic or natural can be used instead of paper. Illustrative, non-limiting examples of suitable materials include paper woven fabrics of nylon, cotton or rayon and the like as well as non-woven fabrics. Optionally, the monitor elements can be coated with a silicone oil to prevent condensation. In that event, however, it is preferred that the oil be room temperature vulcanizable so that the surfaces of the elements will be non-sticky and tack free.

The magnetic material 43 comprised SemiVac 90 Bias material available from Sensormatics, Inc. of Deerfield Beach, Fla. The material 43 was shaped in a four sided polygon with angled ends. The overall surface area of the material 43 was substantially the same as that of the material 41. The material 43 is believed to be parallelogram shaped to focus the shape of the magnetic poles to enhance sensitivity. Optionally, other shapes may be utilized. The material 43 was magnetized by a common magnetizing device believed to comprise a voltage applied to a coil inducing a magnetic field. The magnetizer comprised a No. 19-217 120 Vac 60 Hz. 300 Watts magnetizer, available from Kendrick & Davis, Inc. of Syosset N.Y. The material 43 was moved through the magnetic field in order to magnetize it.

The second paper layer 44 comprised Schleicher & Schuell paper designated by the manufacturer as S&S-593 with a length of about 1.65 inches, a width of about 0.55 inches and a thickness of about 12 mil. (0.012 inches). The second paper layer 44 is optional. Alternatively, the depth of the cavity of the container 50 could be made correspondingly smaller. The first assembly 1 was adhered to the container 50 using Loctite 411 clear adhesive, available from Wilcox Slidders, Inc.

The monitors 10 were assembled into the shape shown in FIG. 8 and placed in the interrogation zone of a Double Checker electronic article surveillance device (Model No. ZB150 available from Sensormatics). No audible signal was heard. The monitors were then subjected to a steam sterilization cycle at a fixed temperature for a fixed period of time. The monitors were then placed in the interrogation zone of the same interrogation mechanism and an audible signal was heard.

Monitors 10 were subjected to steam cycles that typically would cause a Sterigage™ Steam Sterilization Indicator (generally available from 3M Corp.) to visually read "Reject" (e.g. 270 degrees F. for 1 min.). Other monitors 10 were subjected to steam cycles that typically would cause a Sterigage Steam Sterilization Indicator to visually read "Accept" (e.g. 270 degrees Fahrenheit for 3 min.). The monitors were then interrogated by the Double Checker electronic article surveillance device. Table 1 summarizes some results from several tests:

TABLE 1

| AUTOCLAVE TEMP., F. | TIME MIN. | COLOR FRONT | SIGNAL |
| --- | --- | --- | --- |
| 270 | 1 | reject | no |
| 270 | 3 | accept | yes |
| 250 | 10 | reject | no |
| 250 | 18 | accept | yes |

Referring now to FIGS. 10–14, there is shown a second embodiment of sterilization monitor, generally designated by reference character 10A. Like the sterilization monitor 10, the monitor 10A has a strip of magnetostrictive ferromagnetic material 41A, a first spacer strip 42A (e.g. paper), a magnetic material 43A, a second spacer strip 44A (paper), and a container 50A.

Figure 12:
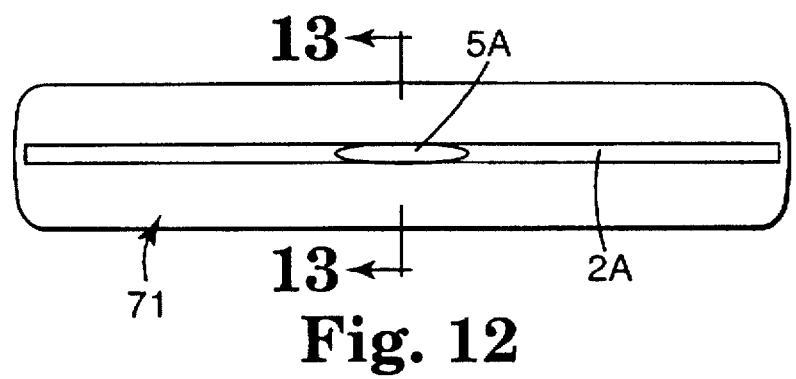
FIG. 12 is a plan view of a portion of a second embodiment of sterilization monitor according to the present invention which includes a meltable organic compound.
Figure 13:
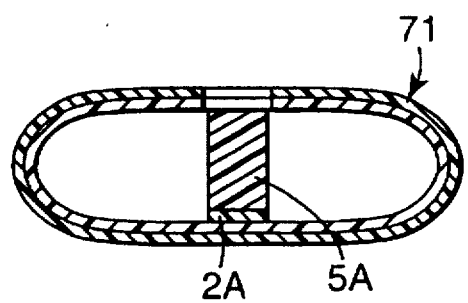
FIG. 13 is an enlarged sectional view taken approximately along lines 13—13 of FIG. 12.
Figure 14:
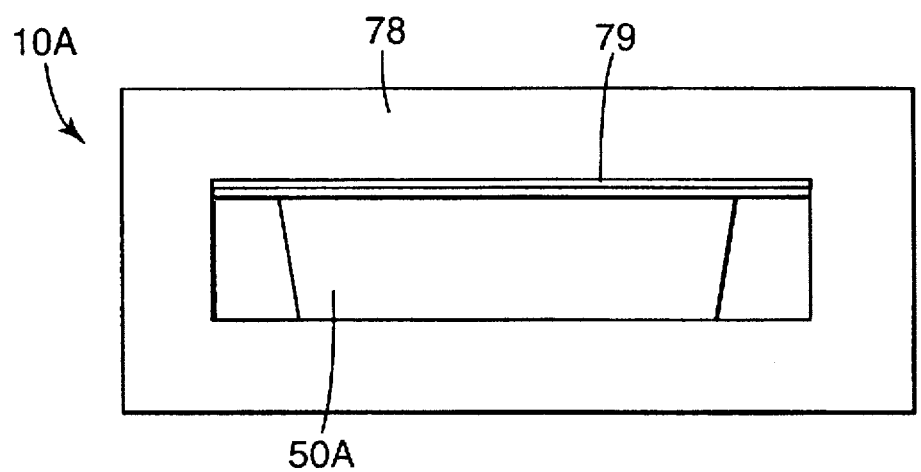
FIG. 14 is a side view of the second embodiment of sterilization monitor according to the present invention.

Referring to FIGS. 12 and 13, the monitor 10A includes a first assembly including a meltable organic material 5A, a wicking strip 2A and a pouch 71. A cover 79 is sealed to the top surface of the container 50A. The cover 79 may comprise a rate controlling film sheet or a substantially impermeable sheet. Optionally, holes may be drilled in the sides of the container 50A to afford the ingress of steam.

Unlike the monitor 10, instead of a spring, the clamping means 77 of the monitor 10 comprises an interference member 78. The interference member 77 places the organic material 5 in an interference fit sufficient to physically hold the magnetostrictive ferromagnetic material 41A such that the magnetostrictive ferromagnetic material is not allowed to resonate when interrogated by the interrogation mechanism.

The interference member 78 is preferably a rectangular O-shaped device with a rectangular opening. The height of the rectangular opening is slightly less than the thickness 84 (see FIG. 11) of the sheet 79, first assembly (e.g. 71, 5A, 2A), elements 41A, 42A, 43A, 44A and bottom of the container 50A. For example the height 84 may be about 0.135 inches while the height of the rectangular opening in interference member 78 may be about 0.125 inches. This slight interference physically holds the magnetostrictive ferromagnetic material 41A so that the magnetostrictive ferromagnetic material 41A is not allowed to resonate when interrogated by the interrogation mechanism. Upon exposure of the monitor 10A to predetermined conditions (e.g. a sterilization cycle), the organic compound 5A melts sufficiently to allow the magnetostrictive ferromagnetic material 41A to resonate when interrogated by the interrogation mechanism.

EXAMPLE 2

Samples of sterilization monitor 10A were constructed. The rate controlling film material comprised 4 mil unoriented polypropylene. The polypropylene is available from Axcess Packaging Inc. of Newark, Del., designated HP285B. The first assembly (FIGS. 12 and 13) was formed by folding the polypropylene over on itself and heat sealing using an impulse sealer along one edge to form a tube having an internal width of about 7/16 inches which is then heat sealed at one end. A wick 2A having dimensions of about ⅛ inches by 1.25 inches comprising Schleicher & Schuell paper designated by the manufacturer as S&S-593 is then slipped into the open ended pouch. A tablet of organic compound 5A comprising about 32 mg. of salicylamide and being about 0.182 inches in diameter and 0.054 inches thick is then positioned into the assembly at about the center of the wick means. The pouch is then evacuated to a vacuum of about 28 inches of mercury, and the remaining open end of the assembly is heat sealed to form a pouch having an internal length approximately equal to that of the wick. A vacuum is drawn to ensure that the internal pressure at sterilization conditions does not rupture the pouch.

Optionally, the pouch may be wrapped in aluminum foil except for an area extending the length of the pouch of about one-eighth of an inch wide. The exposed area of the pouch having no foil coincides with the area in which the organic compound is located. The adhesive utilized was 3M ISO-TAC Acrylic Adhesive.

The container 50A comprises a material which is dimensionally stable at sterilizing conditions. The container 50A is used to contain the pouch and other elements of the monitor 10A. The container 50A was made of 20 mil polyester material and supplied by Mullinex. The container 50A is deep drawn, and subsequently annealed to give it dimensionally stability. The container 50A had apertures to ensure that steam will have access to the pouch. A ferromagnetic element 41A is placed inside of the container 50A. When the assembly has been completed as described the device is tested to insure that the device gives a signal when placed in an interrogation zone. If no signal is emitted the device is not operating correctly, and the cause is determined. With the device operating properly the container 50A is sealed with a film of heated stable polymer 79 e.g., ethylene glycol terphathalte ester polymer (Mylar). The device assembled as described using a 4 mil mylar cover has an overall outer thickness dimension of about 0.135 inches.

The present invention has now been described with reference to several embodiments and examples thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A remotely detectable steam sterilization process monitor for use with an interrogation mechanism capable of interrogating the monitor by providing a pulsed, excitation magnetic field in an interrogation zone, and capable of detecting an identity signal provided by the monitor; the monitor comprising:

a strip of magnetostrictive ferromagnetic material adapted to mechanically resonate when interrogated by the interrogation mechanism, a magnetic material capable of magnetically biasing the strip of magnetostrictive ferromagnetic material to arm the magnetostrictive ferromagnetic material to provide an identity signal such that, after the pulse of the excitation magnetic field of the interrogation mechanism ends, the magnetostrictive material resonates within the magnetic bias provided by the magnetic material in a decaying fashion to thereby provide the identity signal to the interrogation mechanism; and clamping means for physically holding the magnetostrictive ferromagnetic material such that the magnetostrictive ferromagnetic material is not allowed to resonate when interrogated by the interrogation mechanism; the clamping means comprising a meltable compound such that, upon exposure of the monitor to predetermined conditions, the meltable compound melts sufficiently to allow the magnetostrictive ferromagnetic material to resonate when interrogated by the interrogation mechanism.

2. A remotely detectable steam sterilization process monitor according to claim 1 including a wicking means for receiving the compound as it melts.

3. A remotely detectable steam sterilization process monitor according to claim 1 including a rate controlling film.

4. A remotely detectable steam sterilization process monitor according to claim 1 including a container constructed from a material suitable for withstanding a sterilization cycle.

5. A remotely detectable steam sterilization process monitor according to claim 1 wherein the clamping means comprises a spring movable between a first position and second position that is spaced from the first position, wherein, in the first position, the spring provides a bias through the meltable compound which physically holds the magnetostrictive ferromagnetic material such that the magnetostrictive ferromagnetic material is not allowed to resonate when interrogated by the interrogation mechanism, and in the second position, the bias of the spring is released sufficiently to allow the magnetostrictive ferromagnetic material to resonate when interrogated by the interrogation mechanism.

6. A remotely detectable steam sterilization process monitor according to claim 1 wherein the clamping means comprises an interference member placing the meltable compound in an interference fit sufficient to physically hold the magnetostrictive ferromagnetic material such that the magnetostrictive ferromagnetic material is not allowed to resonate when interrogated by the interrogation mechanism.

7. A remotely detectable steam sterilization process monitor according to claim 1 including an assembly which includes an organic compound, a wicking means for receiving the organic compound as it melts, and a rate controlling film.

8. A remotely detectable steam sterilization process monitor according to claim 7 wherein the assembly includes indicia.

9. A remotely detectable steam sterilization process monitor according to claim 7 wherein the assembly includes an aluminum backing and the organic compound is situated between the wicking means and the aluminum.

10. A remotely detectable steam sterilization process monitor according to claim 7 wherein the assembly includes an aluminum backing and the wicking means is situated between the compound and the aluminum.

11. A remotely detectable steam sterilization process monitor according to claim 1 including a water absorbing material situated between the strip of magnetostrictive ferromagnetic material and the magnetic material.

12. A remotely detectable steam sterilization process monitor according to claim 11 wherein the water absorbing material comprises paper.

13. A remotely detectable sterilization monitor for use with an interrogation mechanism, the monitor comprising:

creating means for creating a remotely detectable magnetic response, the creating means comprising a magnetic material of high permeability and low coercivity, said creating means having at least two distinct magnetic states, a first state in which a first remotely detectable magnetic response is created upon a first interrogation, and a second state in which a second remotely detectable magnetic response which is different from the first state is created upon a second interrogation, and clamping and release means for holding the creating means in said first state, said clamping and release means including a spring clamp for holding the creating means in said first state to restrict the creating means from entering the second state, and an organic material which melts upon being heated to a predetermined temperature for changing said creating means from said first to said second state upon melting, wherein the spring clamp is separate and distinct from the magnetic material of high permeability and low coercivity.

14. A remotely detectable sterilization monitor according to claim 13, wherein said creating means comprises a magnetostrictive ferromagnetic material and a magnetizeable material.

15. A remotely detectable sterilization monitor according to claim 13, wherein the organic material comprises a compound selected from the group consisting of 2-chloroacetamide, 2-ethoxybenzamide, benzoic acid, diphenyl succinate, dichlorophenol, dimethyl phenol, benzamide, urea, 1,4 dihydroxybenzophenone, hydroquinone, dioxime, ethylene ester of tuluene sulfonic acid, salicylamide, salicylic acid, and 1,8-octane dicarboxylic acid.

16. A remotely detectable sterilization monitor according to claim 13, wherein said creating means comprises means for changing said first state to said second state upon exposure to a predetermined amount of steam.

17. A remotely detectable sterilization monitor according to claim 13, wherein said creating means includes means for altering pressure from the spring clamp such that the creating means is changed to the second state.

18. A method of monitoring a steam sterilization process using a monitor comprising the steps of:

provideing an interrogation mechanism capable of interrogating the monitor and capable of detecting an identity signal provided by the monitor;

providing an interrogation zone;

providing a monitor comprising a strip of magnetostrictive ferromagnetic material adapted to mechanically resonate when interrogated by the interrogation mechanism, a magnetic material capable of magnetically biasing the strip of magnetostrictive ferromagnetic material to arm the magnetostrictive ferromagnetic material to provide the identity signal, and clamping means for physically holding the magnetostrictive ferromagnetic material such that the magnetostrictive ferromagnetic material is not allowed to resonate when interrogated by the interrogation mechanism; the clamping means comprising a meltable organic compound;

exposing the sterilization monitor to at least a portion of the steam sterilization process to be monitored, such that, after a predetermined exposure to the steam sterilization process to be monitored, the organic compound melts sufficiently to release the clamping means to thereby allow the magnetostrictive ferromagnetic material to resonate when interrogated by the interrogation mechanism;

then interrogating the monitor in the interrogation zone by providing a pulsed, excitation magnetic field at a frequency in the interrogation zone, such that, if the clamping means is released, after the pulse of the excitation magnetic field of the interrogation mechanism ends, the magnetostrictive material resonates within the magnetic bias provided by the magnetic material in a decaying fashion to provide the identity signal to the interrogation mechanism;

detecting the identity signal with the interrogation mechanism; and indicating to a user whether the identity signal was detected by the interrogation mechanism.

19. A method of monitoring a sterilization process using a remotely detectable sterilization monitor without the need to visually inspect the sterilization monitor, the method comprising the steps of:

providing an interrogation mechanism for interrogating the monitor, the interrogation mechanism including an interrogation zone;

providing a sterilization monitor comprising creating means for creating a remotely detectable magnetic response, the creating means comprising a magnetic material of high permeability and low coercivity, the creating means having at least two distinct magnetic states, a first state in which a first remotely detectable magnetic response is created upon a first interrogation, and a second state in which a second remotely detectable magnetic response which is different from the first state is created upon a second interrogation, and clamping and release means for holding the creating means, said clamping and release means including a spring clamp for holding the creating means to restrict the creating means from entering the second state, and a material which melts upon being subjected to sterilization conditions, the spring clamp being separate and distinct from the magnetic material of high permeability and low coercivity;

exposing the sterilization monitor to at least a portion of the sterilization process to be monitored, such that after a predetermined exposure to the sterilization process to be monitored, the compound melts sufficiently to change the creating means from said first to said second state;

then interrogating the monitor in the interrogation zone;

indicating whether the interrogation mechanism detects the second state of the creating means.

* * * * *